United States Patent
Grooms et al.

(10) Patent No.: US 6,652,592 B1
(45) Date of Patent: Nov. 25, 2003

(54) SEGMENTALLY DEMINERALIZED BONE IMPLANT

(75) Inventors: Jamie M. Grooms, Alachua, FL (US);
Kevin C. Carter, Alachua, FL (US);
Thomas W. Sander, Alachua, FL (US);
Dayna Buskirk, Alachua, FL (US);
John Bianchi, Alachua, FL (US)

(73) Assignee: Regeneration Technologies, Inc., Alachua, FL (US)

(*) Notice: Subject to any disclaimer, the term of this patent is extended or adjusted under 35 U.S.C. 154(b) by 0 days.

(21) Appl. No.: 09/417,401

(22) Filed: Oct. 13, 1999

Related U.S. Application Data

(63) Continuation-in-part of application No. 08/958,364, filed on Oct. 27, 1997, now Pat. No. 6,090,998.

(51) Int. Cl.[7] .................................................. A61F 2/36
(52) U.S. Cl. .......................... 623/23.51; 623/16.11; 623/18.11; 606/60
(58) Field of Search .................... 623/11.11, 13.11, 623/13.12, 13.14, 13.17, 17.11, 17.16, 23.63, 23.72, 66.1, 919, 16.11, 18.11, 21, 23.51; 606/60, 61, 72–74, 77; 424/422–423, 426, 548, 549; 427/2.24, 2.26, 2.27; 514/21; 523/113–115

(56) References Cited

U.S. PATENT DOCUMENTS

| | | |
|---|---|---|
| 3,772,709 A | 11/1973 | Swanson |
| 3,875,594 A | 4/1975 | Swanson |
| 3,886,600 A | 6/1975 | Hahn et al. |
| D277,509 S | 2/1985 | Lawrence et al. |
| D277,784 S | 2/1985 | Sgarlato et al. |
| 4,553,272 A | 11/1985 | Mears |
| D284,099 S | 6/1986 | Laporta et al. |
| 4,627,853 A | 12/1986 | Campbell et al. |
| 4,743,259 A | 5/1988 | Bolander et al. |
| 4,759,768 A | 7/1988 | Hermann et al. |
| 4,772,286 A | 9/1988 | Goble |

(List continued on next page.)

FOREIGN PATENT DOCUMENTS

| | | |
|---|---|---|
| EP | 0356112 | 2/1990 |
| EP | 0483944 | 5/1992 |
| WO | WO93/15694 | 8/1993 |
| WO | WO97/25941 | 7/1997 |
| WO | WO97/25945 | 7/1997 |
| WO | WO 99 21515 | 5/1999 |
| WO | WO 99 38453 | 8/1999 |
| WO | WO 00 40179 | 7/2000 |
| WO | WO 01/49219 A1 | 7/2001 |

OTHER PUBLICATIONS

International Search Report, attached to International Application No. PCT/US02/04980, dated Nov. 5, 2002.
Jackson, Douglas W. et al., Biologic remodeling after anterior cruciate ligament reconstruction using a collagen matrix derived from demineralized bone: An expermental study in the goat model, 1996, Am J. Sports Med. 24(4):405–414.

*Primary Examiner*—David H. Willse
*Assistant Examiner*—Urmi Chattopadhyay
(74) *Attorney, Agent, or Firm*—McAndrews, Held & Malloy, Ltd.; Donald J. Pochopien

(57) ABSTRACT

This application provides a novel unitary bone implant having at least one rigid, mineralized bone segment, which may be machined to include threads, grooves, a driver head, perforations, a recess, or a symmetric shape, and a flexible, demineralized segment, which may also be machined to any desired shape prior to demineralization, or after demineralization. The disclosed implant has wide orthopedic applicability, including but not limited to repair or replacement of ligaments, tendons, and joints and for inducing vertebral fusions and fractured bone repair.

7 Claims, 13 Drawing Sheets

U.S. PATENT DOCUMENTS

| | | |
|---|---|---|
| 4,839,215 A | 6/1989 | Starling et al. |
| 4,871,367 A | 10/1989 | Christensen et al. |
| 4,932,973 A | 6/1990 | Gendler |
| 5,053,049 A | 10/1991 | Campbell et al. |
| 5,092,887 A | 3/1992 | Gendler |
| 5,092,896 A | 3/1992 | Meuli et al. |
| 5,133,761 A | 7/1992 | Krouskop |
| 5,171,273 A | 12/1992 | Silver et al. |
| 5,192,322 A | 3/1993 | Koch et al. |
| 5,292,349 A | 3/1994 | Foresti |
| 5,405,390 A | 4/1995 | O'Leary et al. |
| 5,405,400 A | 4/1995 | Linscheid et al. |
| 5,484,443 A | 1/1996 | Pascarella et al. |
| 5,507,813 A | 4/1996 | Dowd et al. |
| 5,676,146 A | 10/1997 | Scarborough |
| 5,919,234 A | 7/1999 | Lemperle et al. |
| 6,123,731 A | 9/2000 | Boyce et al. |
| 6,200,347 B1 | 3/2001 | Anderson et al. |
| 2001/0020188 A1 | 9/2001 | Sander |

3A

3B

7A

7B

7C

7D

SEGMENTALLY DEMINERALIZED BONE IMPLANT

CROSS-REFERENCE TO RELATED APPLICATIONS

This application is a continuation-in-part of application Ser. No. 08/958,364, filed on Oct. 27, 1997, now U.S. Pat. No. 6,090,998.

1.0 FIELD OF THE INVENTION

This invention relates to a device made from segmentally demineralized and appropriately shaped and machined bone for implantation as a ligament, tendon, support or in any other application in which an implant having at least one rigid segment and at least one flexible segment, is required.

1.1 BACKGROUND

There is a continuing need in the art for biologically acceptable ligament or tendon replacements. Various efforts have been made in the art to accommodate this need. For example, in U.S. Pat. No. 5,053,049, a flexible prosthesis of predetermined shape and a process for making said prosthesis was disclosed. According to that disclosure, a flexible biocompatible and non-antigenic prosthesis for replacement of a cartilaginous part was prepared by machining bone into a desired shape corresponding to the shape of a cartilaginous body part to be replaced, demineralization of the bone to impart flexibility, and tanning to reduce antigenicity. There was no disclosure or suggestion of using the demineralized bone as a tendon or ligament replacement.

In U.S. Pat. No. 5,092,887, a method for replacement or augmentation of a damaged fibrous connective tissue was disclosed wherein a ligament made from a segment of bone that had been demineralized was attached between first and second body parts. There was no disclosure or suggestion of machining the bone prior to demineralization to produce fixation ends thereon, and demineralization of only a segment of the thus machined bone to produce a flexible segment, while leaving the machined attachment ends in a fully mineralized and rigid state for fixation directly to bone adapted to receive such fixation ends. The disclosure in the U.S. Pat. No. 5,092,887 with respect to its discussion of background art and methods of demineralization of bone is hereby incorporated by reference.

2.0 SUMMARY OF THE INVENTION

This invention provides a novel bone implant having at least one rigid, mineralized bone segment, which may be machined to include threads, grooves, a driver head, a recess or a symmetric or asymmetric shape, and at least one flexible, demineralized segment, which may also be machined to any desired shape prior to demineralization, or after demineralization.

3.0 BRIEF DESCRIPTION OF THE DRAWINGS

FIG. 1 provides a view of a first embodiment of the implant of this invention in which a rigid bone segment is machined to exhibit threads on each end (FIG. 1A), and which is then demineralized only in the internal section to provide a flexible segment between the machined ends (FIG. 1C); FIG. 1B provides a view of an alternate embodiment in which one end of the implant has a rigid fixation bone block; FIG. 1D shows an end-on view of a cannulated embodiment of the implant of this invention.

FIG. 2 provides a view of a second embodiment of the implant of this invention in which a rigid bone segment is machined to exhibit threads on one end and an attachment hole at the other (FIG. 2A), and which is then demineralized on the attachment hole end of the implant to provide a flexible segment, while retaining the threaded segment as a rigid member (FIG. 2B). A partial cannulation of the implant is shown in end-on (FIG. 2C), top (FIG. 2D) and side views (FIG. 2E).

FIG. 3 provides a view of a third embodiment of the implant of this invention in which a rigid bone segment is machined to exhibit a fixation block at each end of the implant (FIG. 3A), and which is then demineralized between the two ends to provide a flexible segment between the machined fixation block ends (FIG. 3B).

FIG. 4 provides a view of a fourth embodiment of the implant of this invention in which a rigid bone segment is machined to exhibit a fixation block at one end and an attachment hole (FIG. 4A) or several holes or perforations (FIG. 4B) at the other, and which is then demineralized at the end bearing the attachment hole(s) (FIGS. 4C and 4D) to provide a flexible segment, while retaining the fixation block end as a rigid member.

FIG. 5 shows one method of implantation of the implant of this invention in which fixation screws are utilized to retain the implant of this invention in place either by locking the implant in place through holes in the rigid segment of the implant (FIG. 5A), or by locking the implant into place at the rigid end of the implant via a tapped recess (FIGS. 5B and 5C).

FIG. 6 shows an embodiment of this invention in which the implant is a femoral ring (FIG. 6A) in which the upper and lower ends of the ring are retained in a rigid, mineralized state and which may be machined to exhibit a thread or a groove, and the internal segment of the implant is demineralized to exhibit a soft spongy layer to provide flexible support upon insertion of this embodiment of the invention between adjacent vertebral bodies; alternatively, the upper, lower or both segments may be demineralized and the internal segment may be retained in a mineralized state; FIG. 6B shows this implant having angled faces; FIG. 6C shows this implant machined as a wedge.

FIG. 7 shows various cross-sections (FIG. 7A, spherical; FIG. 7B, elliptical; FIG. 7C, rectangular; FIG. 7D, cross-shaped) for the mineralized or demineralized segment of the implant of this invention.

4.0 DETAILED DESCRIPTION OF THE PREFERRED EMBODIMENTS

This invention provides a biologically acceptable ligament, tendon, support or other implant for replacement of damaged ligaments, tendons, vertebral disks and the like, wherein there is a need for an implant having both a rigid machined portion or segment as well as a flexible, demineralized portion or segment. According to one embodiment of this invention, a segment of preferably cortical bone is machined into a desired shape, with at least one end being machined so as to provide a means for fixation of that end directly to a bone machined in a complementary fashion.

Figure 1:
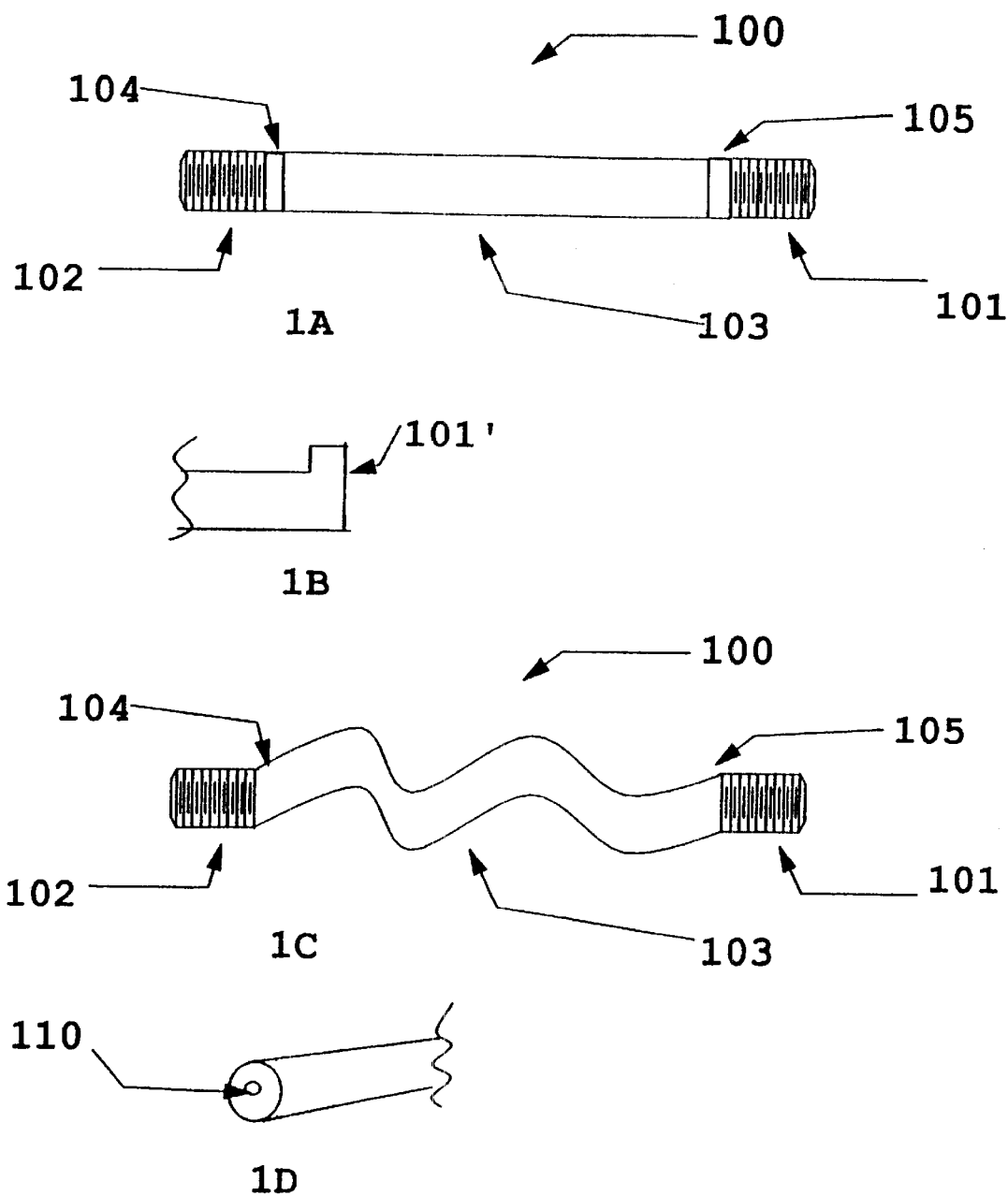

Referring to FIG. 1A, a first embodiment of the implant of this invention 100 is shown in which the ends 101 and 102 of the implant are machined so as to exhibit a thread, and the bone to which the implant is to be affixed is tapped to exhibit a receiving thread complementary to the thread on the implant end. Alternatively, the threaded ends 101, 102 may be self-tapping, thereby eliminating the need to tap the receiving bone. A simple hole, of a diameter slightly smaller than the diameter of the threaded implant ends, may be drilled or produced by like means to receive the threaded implant end. An internal segment 103 of the implant is demineralized to provide a flexible segment of the implant, while transition zones 104, 105 are provided wherein the level of mineralization of the bone gradually changes from a fully mineralized to a demineralized state. In a preferred version of this embodiment of the invention, the two ends 101, 102 of the implant are machined to exhibit threads such that clockwise or counterclockwise rotation of the entire implant results in simultaneous insertion of both ends of the implant or extraction of both ends of the implant into or out of complementarily machined bones to which the implant is to be affixed, without kinking of the flexible segment 103 of the implant. In FIG. 1B, an alternate embodiment is shown wherein one of the ends, 101', is not threaded, but is machined to any desirable shape, such as a fixation block, such that the threaded end 102 may be threaded into the receiving bone, while the fixation block 101' is affixed in place by interference screws or like means known in the art. In yet a further embodiment, shown in FIG. 1D, the entire implant is machined so as to exhibit a cannulation 110 throughout its length or a portion thereof. In this fashion, the implant may be inserted over a guide-wire or like guide means. Alternatively, the aspect 110 may be an internal thread capable of receiving a threaded retention screw. It will be recognized that features disclosed for this embodiment or any of the other embodiments of the invention may be applied to other embodiments of this invention, to produce embodiments exhibiting a variety of combinations of different features disclosed for each of the individually disclosed embodiments.

Figure 2:
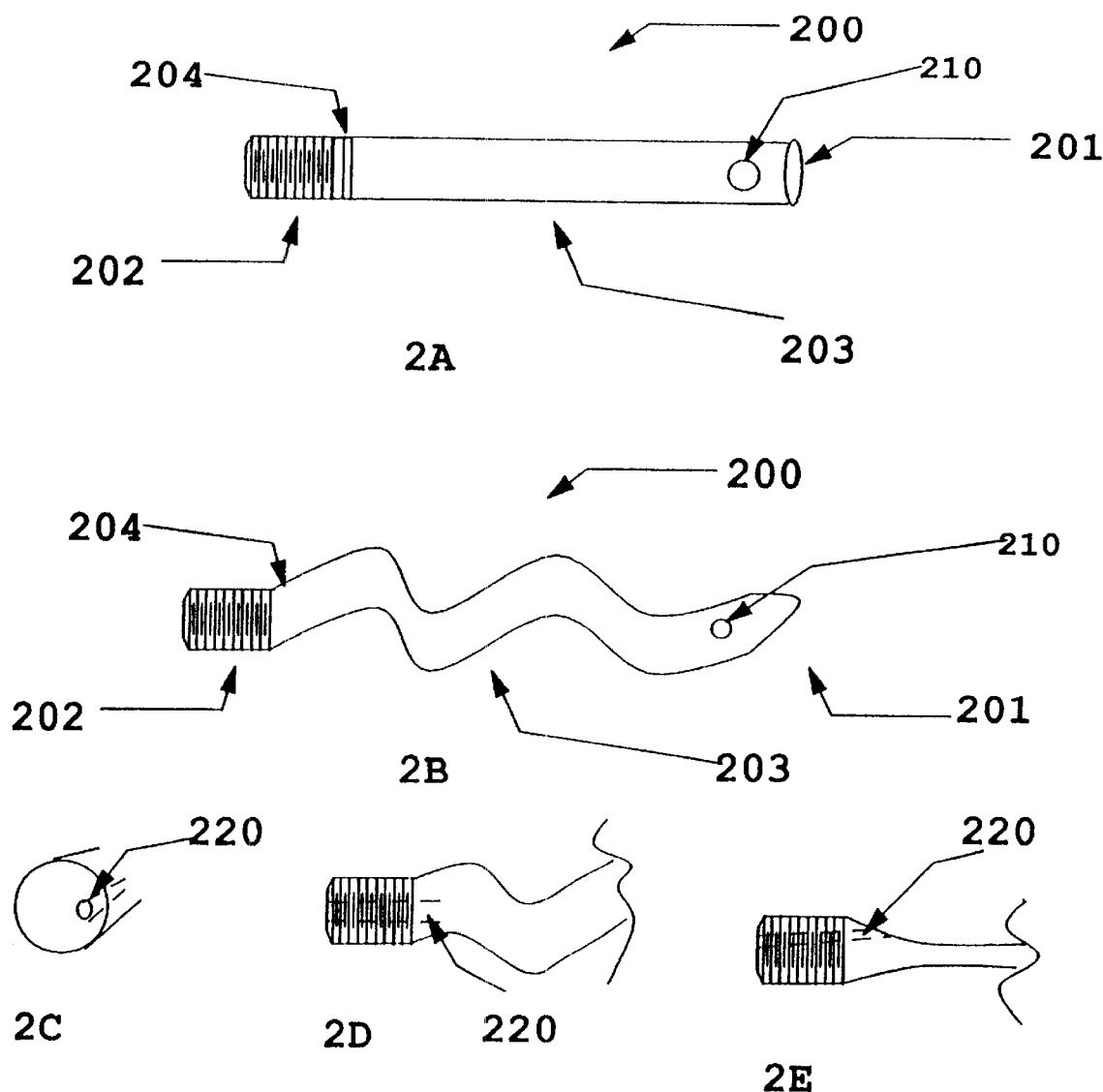

In a further embodiment of this invention 200 shown in FIG. 2, only one end 202 of the implant 200 is machined to exhibit a thread or another machined feature, while the other end 201 may be machined to exhibit a fixation hole 210 or a similar feature, which permits for suturing or otherwise fixing that end to a ligament or a tendon. A transition zone 204 from a mineralized to a demineralized state is provided, as is a flexible segment of the implant 203. In FIGS. 2C–E, there are shown an end-on view, a side view and a top view, respectively. In this embodiment of the invention, an optional cannulation 220 is shown, permitting threading of the machined portion 202 of the implant over a guide-wire, for example, while not interfering with the flexible, demineralized segment 203 of the implant.

Figure 3:
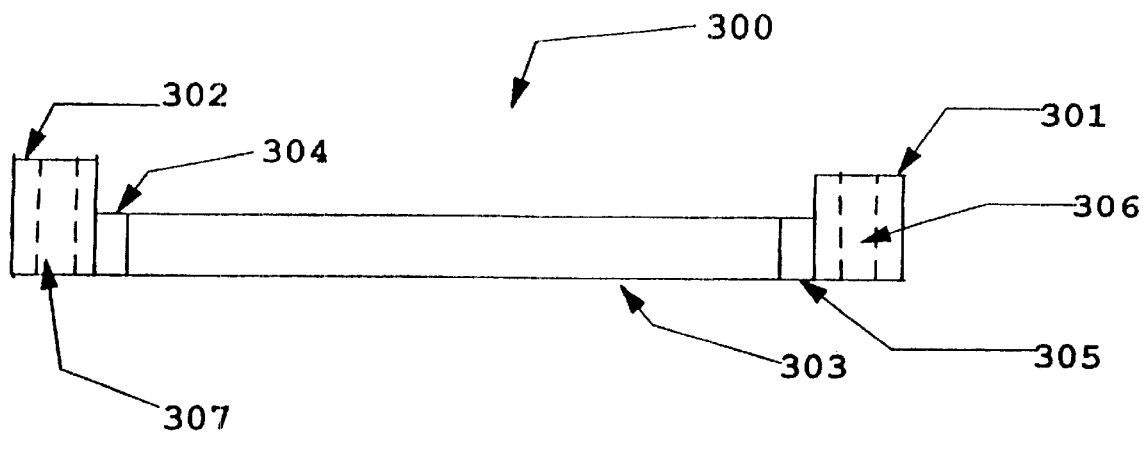
Figure 3:
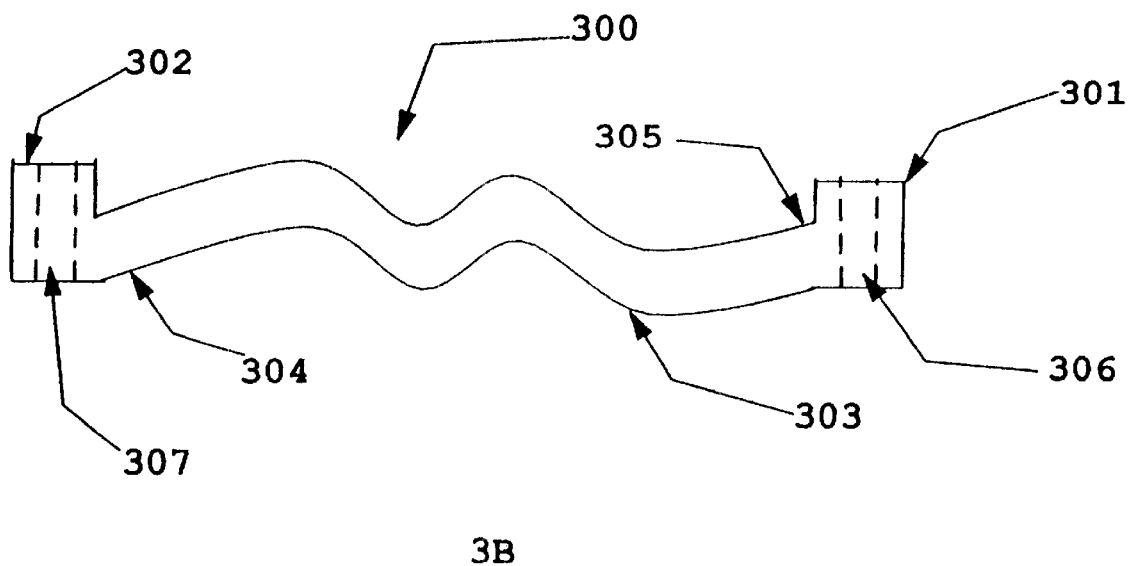

In a further embodiment 300 of this invention shown in FIG. 3, the implant may be used to replace a ligament. In this embodiment, two transition zones 304, 305 from the flexible segment 303 to terminally mineralized fixation blocks 301, 302 are provided. The fixation blocks 301 and 302 each have a canal 306, 307 machined therein for receiving a fixation screw or pin. The mineralized sections 302, 303 may be machined into any desired form of an anchoring fixture. The anchoring fixture may contain a screw thread, a hole for receipt of an anchoring pin or an anchoring screw, or a screw that rotates within a sleeve.

Figure 4:
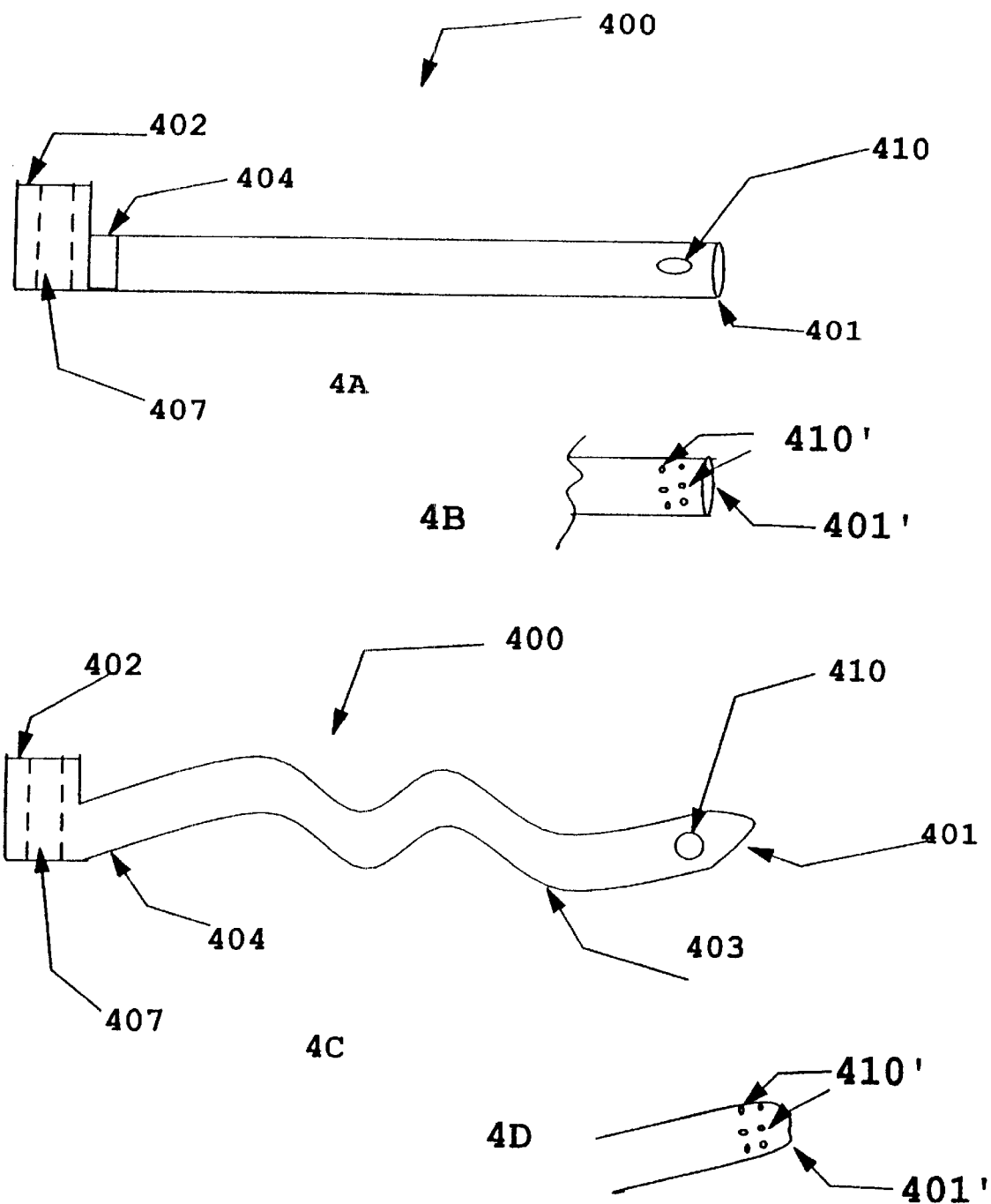

In the embodiment 400 shown in FIG. 4A, the implant is used for repair or replacement of a tendon. In this embodiment, only one end 402 of the implant 400 is machined for fixation in a bone, and the second end 401 of the implant is adapted to a variety of shapes, terminating in a means, such as a threadable hole 410, for fixation of that end to bone, muscle, tendon or ligament. In an alternate embodiment shown in FIGS. 4B and 4D, the end 401' is machined to exhibit a plurality of holes or perforations, 410', such that end 401' may be sutured to a receiving biological structure, such as a muscle, ligament, tendon, bone or the like.

Figure 5:
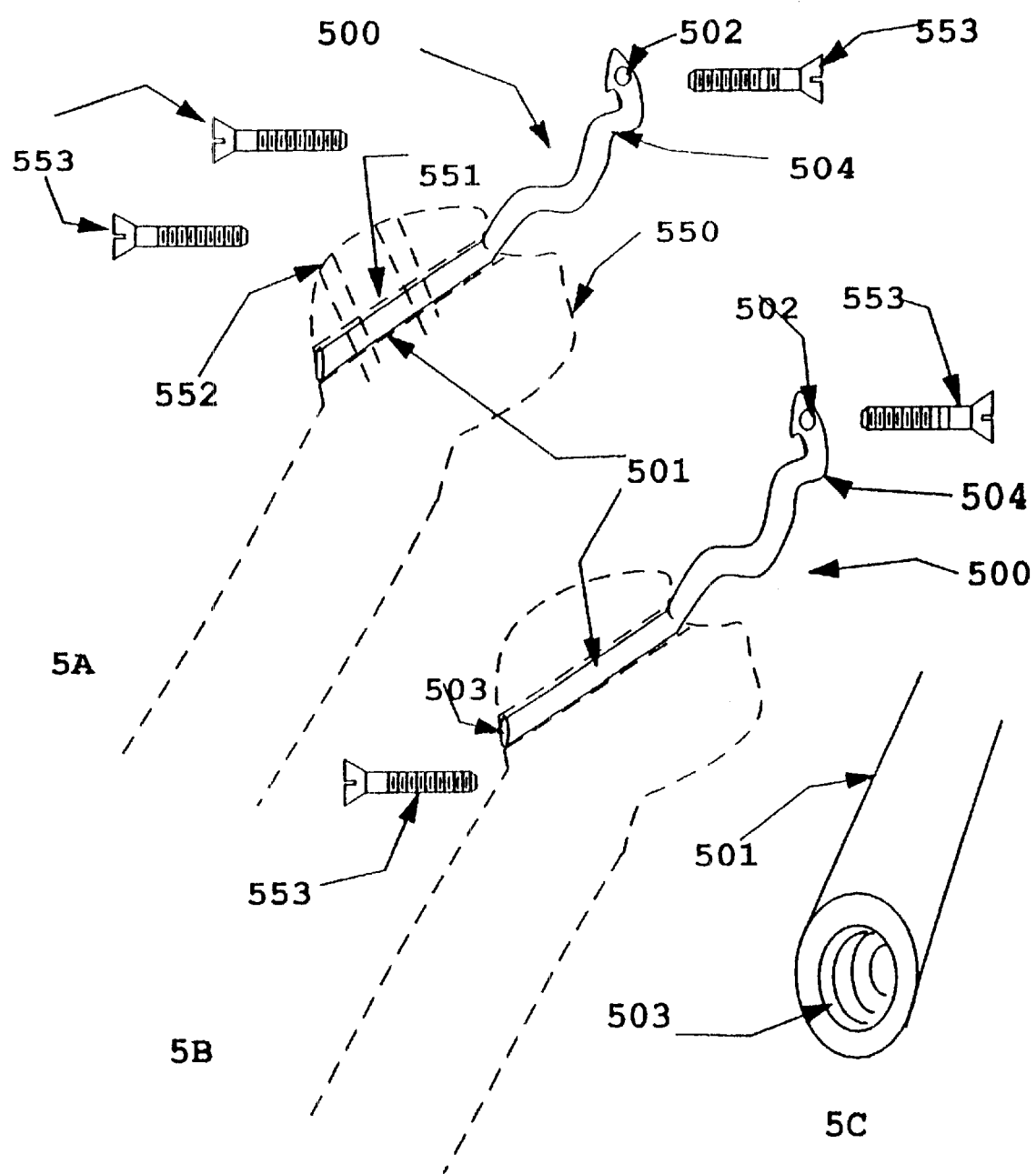

In FIG. 5, one method of implantation of the implant 500 of this invention is shown in which fixation screws 553 are utilized to retain an embodiment of the implant 500 of this invention in a machined slot 551 in a bone 550 either by locking the implant in place (FIG. 5A) through holes 552 in the rigid segment 501 of the implant (FIG. 5A), or by locking the implant into place at the rigid end 503 of the implant via a tapped recess (FIGS. 5B and 5C). The other end of the implant 504 is demineralized, and is thus flexible, and terminates in a hole 502 or other fixation means by which that end of the implant is attached to bone, tendon, ligament or muscle. As noted above, section 501 could be threaded, end 502 could be retained in a mineralized state and could be shaped as a fixation block for retention by an interference screw, or threaded. In addition, the implant 500 may be cannulated, with the recess 503 continuing through the entire length of the implant, or some portion thereof.

Figure 6A:
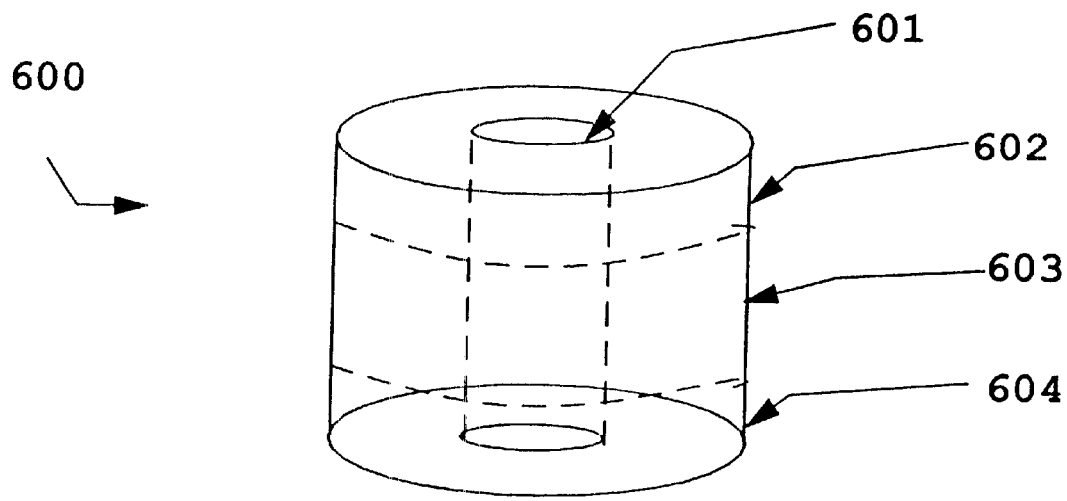

FIG. 6A shows an embodiment of this invention in which the implant 600 is a femoral ring member or a portion thereof wherein the upper and lower ends or faces 602, 604 are retained in a rigid, mineralized state and which may be machined to exhibit a thread or a groove by means known in the art (see WO 97/25945, hereby incorporated by reference for this purpose). The internal segment of the implant 603 is demineralized to exhibit a soft spongy region to provide flexible support upon insertion of this embodiment of the invention between, for example, adjacent vertebral bodies. An internal canal 601 is shown in the femoral ring, which derives from the natural intramedullary canal of the bone from which the femoral ring is obtained by substantially planar, parallel cross-cuts across the diaphysis of a femur or like long bone. Alternatively, a transverse cut to form a dowel which is then segmentally demineralized is also contemplated. The canal may be left open or filled with osteogenic factors, including but not limited to autologous bone or marrow. Alternatively, the canal may be filled with a carrier and growth factors, including but not limited to bone morphogenetic proteins, demineralized bone matrix (DBM), or any inert or biologically active substance considered beneficial for insertion into the spine to assist in support thereof or for fusion of adjacent vertebrae.

Figure 6B:
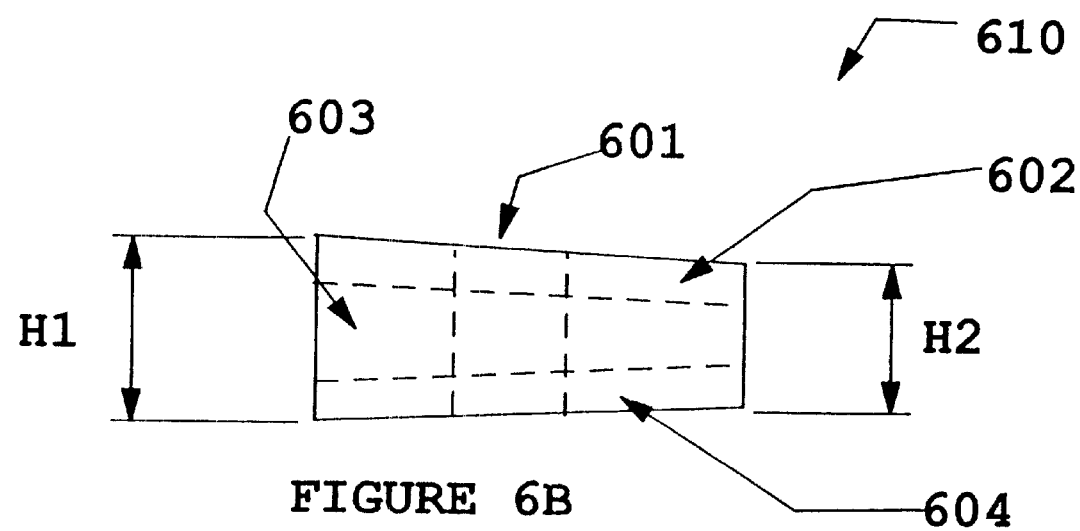
Figure 6C:
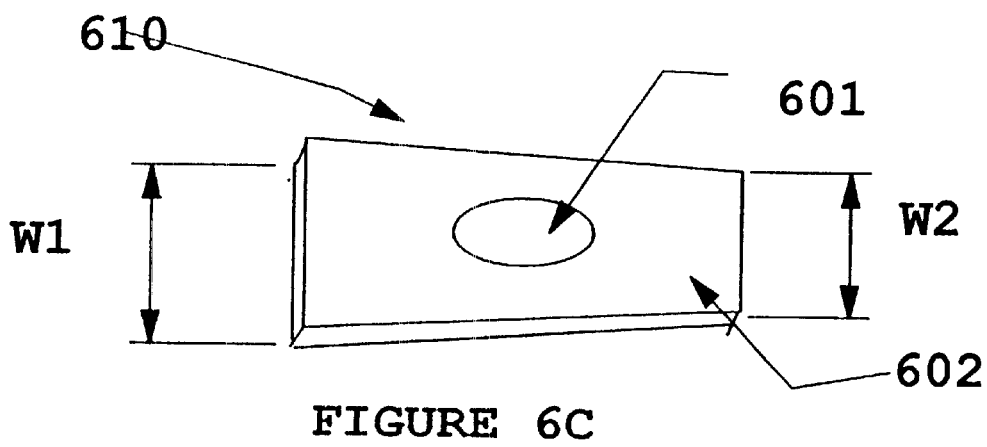

Furthermore, the canal may retain the natural architecture of the intramedullary canal or it may be scraped out or otherwise modified. Those skilled in the art will appreciate that in this embodiment of the invention, the upper end 601, the lower end 604, or both may be demineralized, while the internal segment 603 of the implant may be maintained in a mineralized state. It will further be appreciated that the upper 602 and lower 604 faces of the implant may not be parallel, but rather may slope toward each other, as shown for embodiment 610 in FIG. 6B, such that H1 is greater than H2. Furthermore, the upper and lower faces may exhibit curvature and external features, such as grooves, pits or protrusions to assist in the retention of the implant when inserted between adjacent vertebrae. In an embodiment comprising sloping upper and lower faces, the slant of the upper and lower faces should be such that the natural lordosis of the spinal segment into which the implant is inserted is maintained. It will further be appreciated that the shape of the implant may include a substantially circular, elliptical, rectangular or like shape. As shown in FIG. 6C, the implant may comprise a portion of the femoral ring, exhibiting a greater width W1 and a lesser width W2. Furthermore, the upper surface, lower surface or both surfaces may comprise features such as grooves, pits, indents, teeth or protrusions to inhibit slippage or expulsion of the implant.

The implant of this invention comprising a segmentally demineralized bone comprising at least one mineralized portion or segment, and at least one flexible, demineralized portion or segment is produced by machining a piece of preferably cortical bone into any desired shape. The bone is preferably chosen to be strong cortical bone, such as from the femur, tibia, fibula, radius or ulna. The source of the donor bone may be autograft, allograft or xenograft bone, with the appropriate cautionary steps known in the art being taken in each case to prevent introduction into the recipient of pathogenic or antigenic agents.

After appropriately shaping the implant bone stock, a segment of the implant is preferably machined to exhibit a thread or like fixation means whereby the implant may be directly affixed to recipient bone machined in a complementary fashion. That segment of the implant is retained in a mineralized state, by appropriately protecting that segment of the implant with any protective device, such as with parafilm, a rubber or latex covering, plastic wrap, and the like. The remaining segment of the implant is then demineralized according to methods known in the art. For example, in the embodiment 100 of this invention shown in FIG. 1A, both ends 101, 102 may be inserted into rubber stoppers spanning the transition zones 104, 105, and the internal segment 103, is exposed to an acid solution of sufficient strength to leach the minerals from that segment of the bone. A 5% acetic acid solution or a 1 N hydrochloric acid solution may be employed, and the implant checked periodically for the desired level of flexibility of the internal zone 103. It is important that an excessively high concentration of strong acid not be employed for this process, as this will result in cleavage of the peptide bonds of the collagenous matrix within which the minerals are deposited. Accordingly, HCl concentrations of between about 0.1N to 2N are acceptable, with the period of exposure to acid being increased for the lower acid concentrations and decreased for the higher acid concentrations. Likewise, depending on the strength of the acid used. The transition zones 104, 105 are formed by diffusion of the acid into and diffusion of the minerals out of the bone in that segment of the implant covered by the protective covering. By varying the degree of demineralization, the properties of the implant of this invention may be altered to provide optimal strength and flexibility, as required for the particular application for which the implant is to be employed.

Figure 9A:
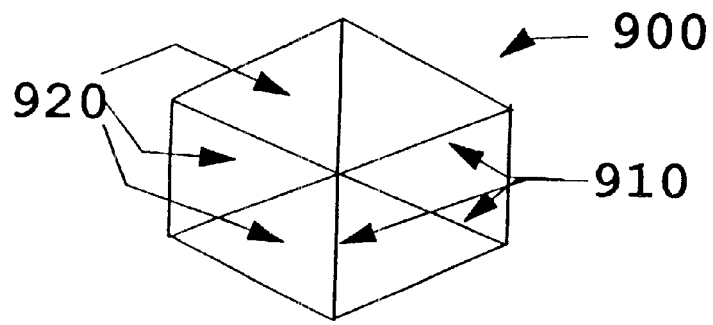
FIG. 9 depicts a flexible implant according to this invention for contoured repair of bone defects, including but not limited to craniomaxillofacial defects, including a first "pizza-shaped implant" (FIG. 9A), a second "pizza-shaped implant" (FIG. 9B), and a wrap implant having alternating mineralized and demineralized segments (FIG. 9C).
Figure 9B:
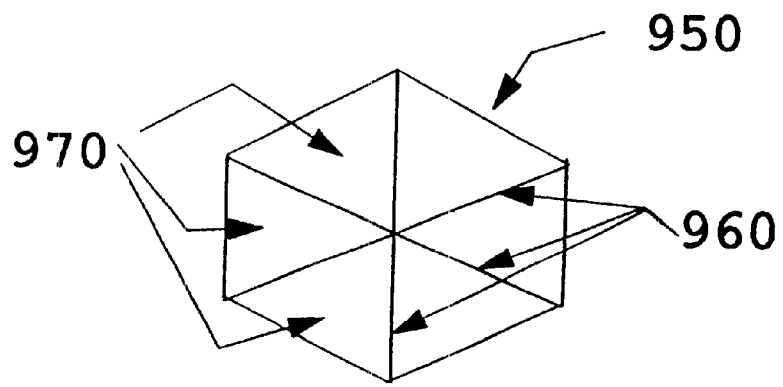
Figure 9C:
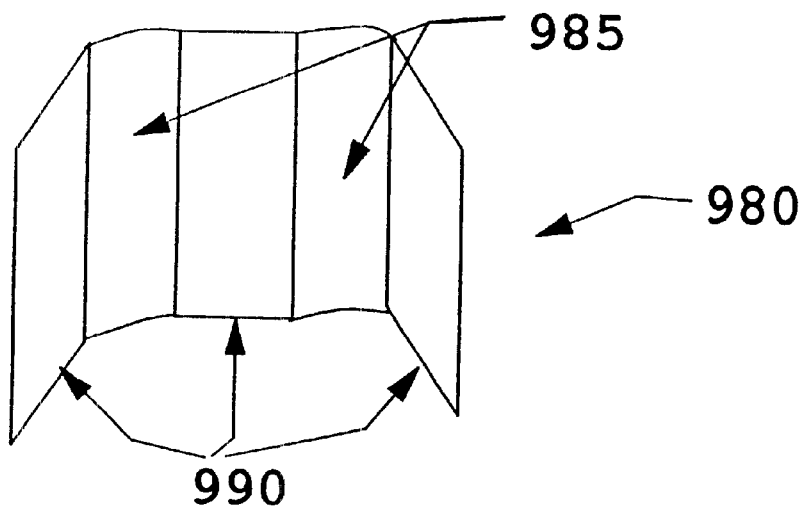

The implant of this invention may be prepared by appropriately masking portions of the implant, using a tape, rubber, latex or any other material which may be adhered to any portion of the bone, to prevent demineralization of portions thereof. Accordingly, in one embodiment of this invention, the implant is produced by masking portions of a flat segment of cortical bone, to form a striated "pizza-slice-shaped" implant device, as shown in FIG. 9. According to this embodiment of the invention, a shape, such as a substantially hexagonal piece of cortical bone 900 is demineralized after application of masking means 910 such that intermediate sections 920 are demineralized while zones of mineralized bone remain where masked at 910. Alternatively, as shown in FIG. 9B, an implant 950 is produced wherein zones 960 are protected from the demineralizing agent (acid, chelating agents, and the like), while areas 970 are not protected. The result is a pizza-slice-shaped implant 950 having flexible hinge portions with mineralized pizza-slice-shaped portions 960 which retain mineral and rigidity. An implant such as 900 or 950 has application, for example, in the repair of craniofacial or craniomaxillofacial defects, among other possible applications. As a result, what is produced is either an implant which comprises a plurality of adjacent mineralized triangular segments, the apex of each triangle meeting at a common point and the sides of each triangle except the base opposite the apex being joined to each other through a demineralized hinge, or an implant which comprises a plurality of adjacent demineralized triangular segments, the apex of each triangle meeting at a common point and the sides of each triangle except the base opposite the apex being joined to each other through a mineralized hinge. It will be understood that other shapes or forms of alternating mineralized and demineralized bone may also be produced and used according to this invention. Thus, for example, a "bone-wrap" 980 shown in FIG. 9C may be produced from a sheet of cortical bone with alternating mineralized 990 and demineralized 985 zones for wrapping around a piece of fractured bone, for example. In this way, the mineralized portion of the bone-wrap acts as a splint while the flexible, demineralized portion of the bone-wrap permits the implant to wrap around the fractured bone segment. The flexibility of the implant permits the implant to be contoured to the surface of a bone defect area to repair such defect. Naturally, based on this disclosure, those skilled in the art will appreciate that implants of a wide variety of shapes, sizes and applications may be produced in a similar manner wherein a portion of the implant retains a rigid mineralized portion and a portion of the implant is at least partially demineralized to produce a flexible portion of the implant. Thus, sheets of bone, partially demineralized wrapping sheets and the like are all variations on this theme which come within the scope of the instant invention.

In a further aspect of this invention, a partial demineralization of the surface of bone implants has been found to be beneficial in that modification of the stress-fracture behavior of the bone may thus be achieved. Accordingly, depletion of up to about 25 percent of the natural bone mineral may be achieved by limited demineralization to break up the bone crystal structure in the partially demineralized portion of the implant. As a result, reduction in the variability of the stress load at which bone fractures upon stress of the bone has been noted, even when as little as a one percent reduction in the bone mineral content is used. This observation may be combined with embodiments of the implant of this invention wherein a portion of the implant is maintained in a rigid, mineralized state, while at least one portion of the implant is demineralized or partially demineralized.

It will further be appreciated that the implant of this invention may be further treated by tanning or other means known in the art to reduce the antigenicity of the implant. For example, glutaraldehyde treatment (see U.S. Pat. No. 5,053,049, hereby incorporated by reference for this purpose), may be used. Alternatively, or in addition, the implant may be subjected to treatment with chaotropic agents, including but not limited to urea, guanidine hydrochloride, combinations thereof and like agents, to remove noncovalent immunogens. Treatment with reducing agents, detergents, chelating agents and the like may also be beneficially applied, depending on the nature of the bone implant and its source. For example, where xenograft bone is used as the material for implant production, reduction in the antigenicity of the bone becomes much more important than if autograft or allograft bone is used.

Figure 7:
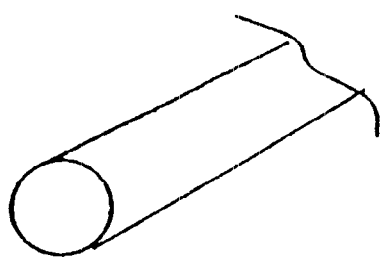
Figure 7:
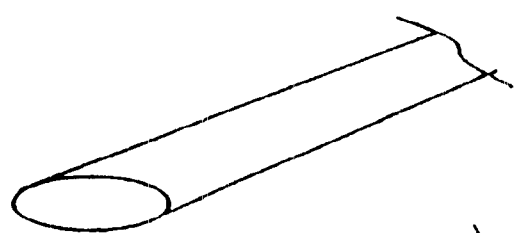
Figure 7:
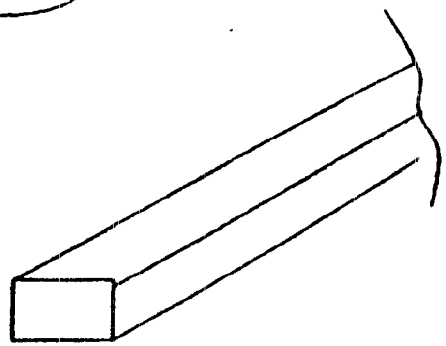
Figure 7:
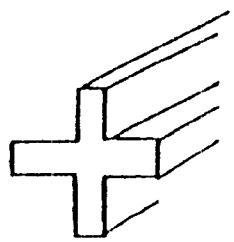

In FIG. 7, various cross-sectional shapes of the implant of this invention are shown. Thus, in FIG. 7A, a cylindrical cross-section is shown. It will be recognized that various diameters, from as small as 0.5 mm or smaller to as large as 10 mm, or in certain applications, even larger, may be desirable. In FIG. 7B, an oval cross-section is provided. In FIG. 7C, a flat cross section is provided. In FIG. 7D, a cross-shaped cross-section is provided. Those skilled in the art will recognize that the disclosure of this invention permits for essentially any desirable shape to be generated for the flexible or rigid segments of the implant of this invention, and such variations come within the scope of this disclosure and the appended claims. In forming the various cross-sectional shapes suggested herein, it is desirable that a smooth transition occurs between the rigid end(s) of the implant and the flexible segment. This is accomplished by appropriately machining the end(s) such that a taper into the flexible segment occurs, and by carefully controlling the demineralization process to ensure a graded demineralization from the fully mineralized segment to the demineralized segment.

It will further be understood from the foregoing disclosure that the implant of this invention may be appropriately fashioned for a wide diversity of applications. For example, an implant of this invention may be applied to repair of ligaments or tendons in the hand, elbow, knee, foot, ankle or any other anatomical location as needed. Furthermore, the implant of this invention may be applied to replacement any of a variety of joints. Methods and implant shapes known in the art for joint replacement, (see, for example U.S. Pat. Nos. 4,871,367; Des. 284,099; Des. 277,784; Des. 277,509; 3,886,600; 3,875,594; 3,772,709; 5,484,443; 5,092,896; 5,133,761; 5,405,400; and 4,759,768; all of which are herein incorporated by reference for their teachings of various considerations applicable to joint prosthetic implants), may be fashioned according to and replaced by the implant of the instant disclosure. Thus, in one embodiment of this invention, a piece of cortical bone is shaped so as to form a surgically implantable prosthetic joint having a load distributing flexible hinge, analogous to that disclosed in U.S. Pat. No. 3,875,594 (which was made from molded silicone rubber). According to this embodiment of the invention, a prosthesis is formed consisting of an enlarged midsection, and a pair of oppositely projecting distal and proximal stem portions. The volar aspect of the midsection is machined to exhibit an indent or transverse channel extending across its width, to form the flexible hinge upon demineralization of the midsection. The midsection, intended to act as the hinge, is demineralized, and the mineralized extremities of the implant are retained in a mineralized state for insertion of each end into the intramedullary space of the bones adjacent to the joint which the implant replaces. The mineralized extremities are machined to exhibit a thread or a ratcheting tooth structure, such that upon insertion of each end into the intramedullary space of the adjacent bones, the end is fixed in place. Since the ends are made from bone, the natural process of fusion between the implant and the bone into which it is inserted occurs over several weeks, thus permanently fixing the prosthesis into position and preventing any movement of the ends of the implant. Implants according to this embodiment of the invention may be used, for example, to replace metacarpophalangeal joints, proximal interphalangeal joints and the like. Accordingly, this invention represents a significant advance in the art as it provides a natural alternative to currently employed metallic, hydroxyapatite, silastic, silicone or like elastomeric materials for joint arthroplasty.

Figure 8A:
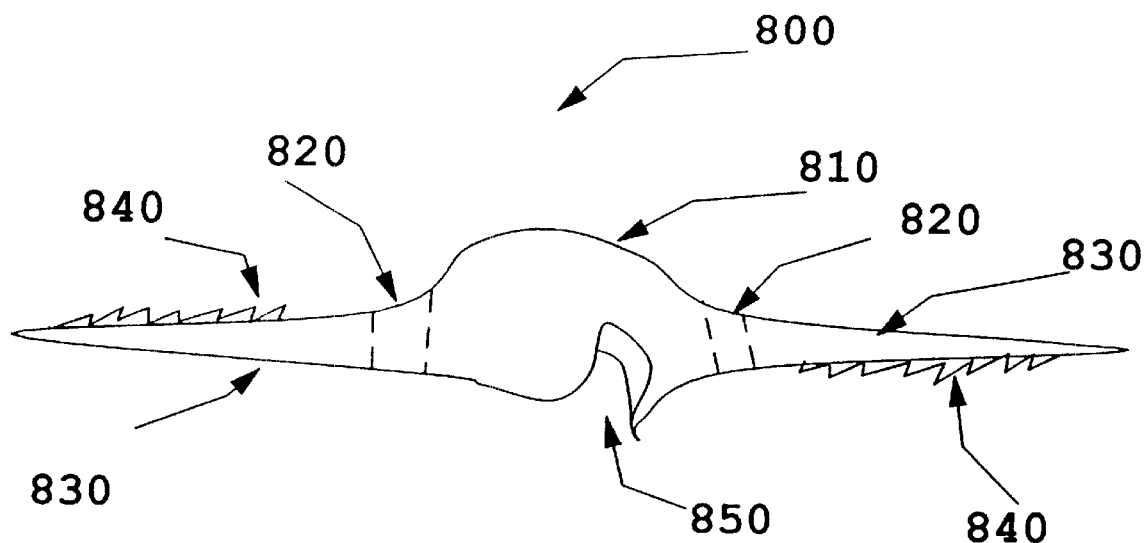
FIG. 8 depicts one embodiment of a prosthetic joint according to this invention having pointed projections for replacement of a joint (FIG. 8A) or for insertion between vertebrae (FIG. 8B).
Figure 8B:
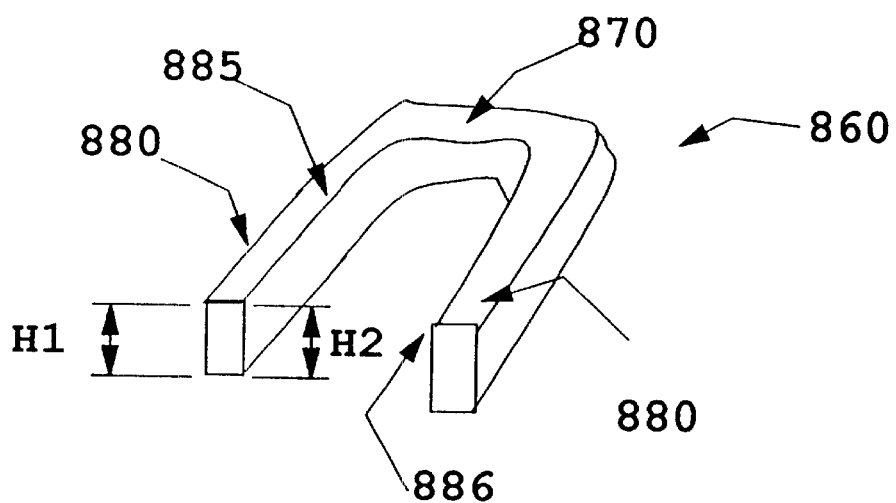

In FIG. 8A, there is provided one diagrammatic representation of an implant of a prosthetic joint according to this invention and which may be prepared according to the concepts central to the instant invention. The implant 800 has an enlarged midsection 810 which is demineralized up to and including a portion of the transition segment 820. On either side of the midsection 810 are mineralized projections 830 adapted for insertion into the intramedullary canals of bones adjacent to the joint which the implant 800 replaces. A groove or channel 850 is provided to act as the hinge and to allow being motion of the joint according to principles described in U.S. Pat. No. 3,875,594, herein incorporated by reference for this purpose. Optionally the projections 830 may exhibit an external feature designed to enhance retention of the implant in the intramedullary spaces. In the embodiment shown in FIG. 8A this feature is shown as a tooth-like serration 840 which may be machined into an upper or lower aspect of each projection 830 or which may project around the circumference of the projections. Alternate external features which may aid in retention of the implant include holes through which retention pins may be inserted, grooves, ribbings and the like. The demineralized midsection 810 permits the implant 800 sufficient flexibility to allow that portion of the implant to act as a joint, while the projections 830 fuse with the bone into which they are inserted to form a permanent fixation. It will be appreciated that, as shown in FIG. 8B, an implant 860 similar to that shown in FIG. 8A may be implemented for inducing spinal fusion, whereby an intermediate section 870 is demineralized while extension thereof 880 are retained in a mineralized state. In this embodiment, there is no need for an enlarged internal segment of demineralized bone, although there may be application in which it is desirable for the height H1 to be greater or smaller than the height H2. For example, where the natural lordosis of the spinal segment into which the implant 860 is to be inserted, the height H1 may preferably be greater than the height H2. In addition, the upper surface 885, the lower surface 886, or both may comprise features such as grooves, pits, or projections which help retain the implant between vertebrae when inserted into an intervertebral space.

Figure 10A:
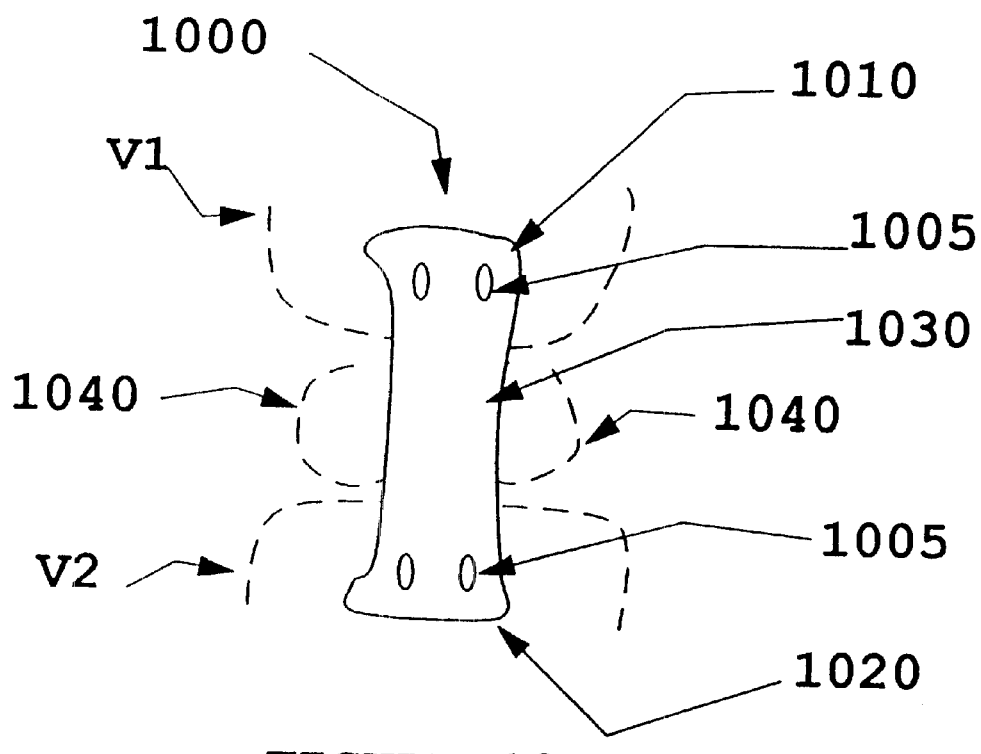
FIG. 10A depicts a first embodiment and FIG. 10B depicts a second embodiment of an anterior longitudinal ligament replacement for limiting motion between adjacent vertebrae to be fused.
Figure 10B:
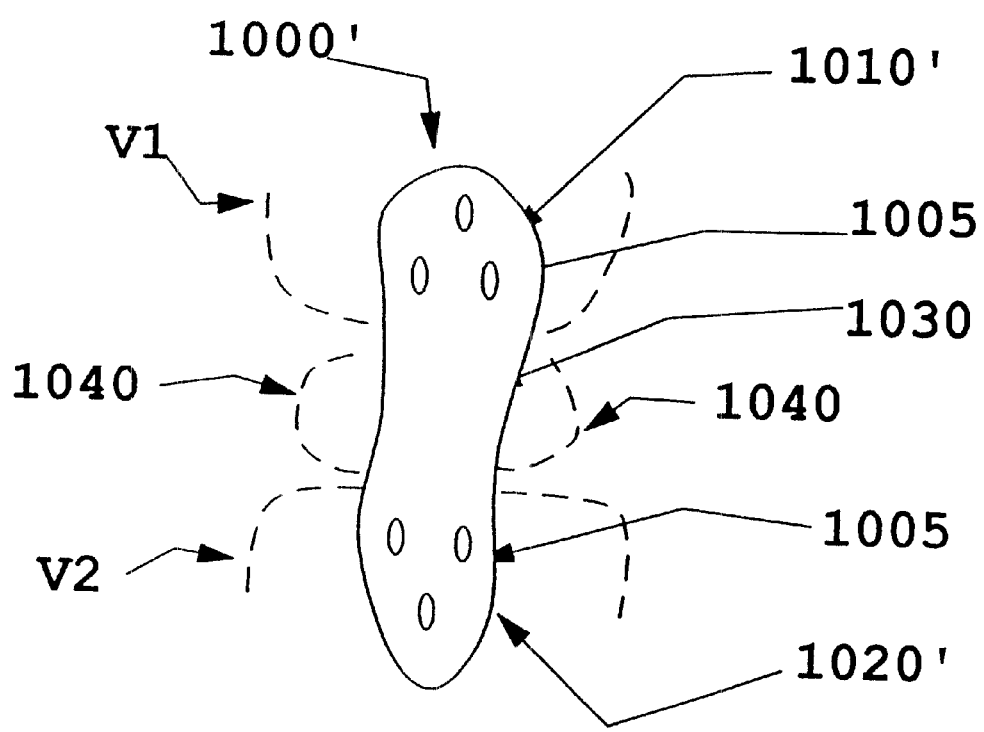

Further application to which the instant invention may be applied include production of a segmentally demineralized anterior longitudinal ligament (ALL) for stabilization of spinal motion segments anteriorly after removal or ligation of an anterior longitudinal ligament. An ALL produced according to the method of this invention may be used to advantage to prevent expulsion of interbody grafts, and is preferably affixed to the vertebral bodies with screws, pins, staples or anchors of various types know in the art or heretofore developed. As a result, lumbar extension is reduced, thereby providing a more stable environment to promote fusion. In FIG. 10, there is provided one embodiment 1000 of the ALL according to this invention. The ALL 1000 is prepared from the distal femur or other flat cortical surface, such as the proximal humerus or tibia. A top portion 1010 and a bottom portion 1020 is retained in a mineralized state, or is only partially demineralized, or is surface demineralized to modify the stress-fracture behavior of that portion of the implant. The top portion 1010 and the bottom portion 1020 each have a series of holes 1005 by means of which the ALL is affixed to a superior vertebra V1 and an inferior vertebra V2. An intermediate section, 1030 is demineralized, to an extent sufficient to permit that segment of the ALL to have a degree of flexibility. In this fashion, while permitting a slight amount of motion, the ALL substantially restricts motion at the vertebral segment spanned by the ALL. Also shown in outline is a pair of interbody implants 1040 inserted between superior vertebra V1 and inferior vertebra V2, spanned by the ALL, in order to induce fusion between V1 and V2. In FIG. 10B, there is shown a further embodiment 1000' of the ALL of this invention which is identical in all respects to the implant shown in FIG. 10A, but wherein this embodiment has an enlarged upper segment 1010' and lower segment 1020' for affixation to the vertebrae V1 and V2. It will be appreciated that the precise shape of the ALL is not critical. Furthermore, the ALL may span more than two vertebrae.

Figure 11:
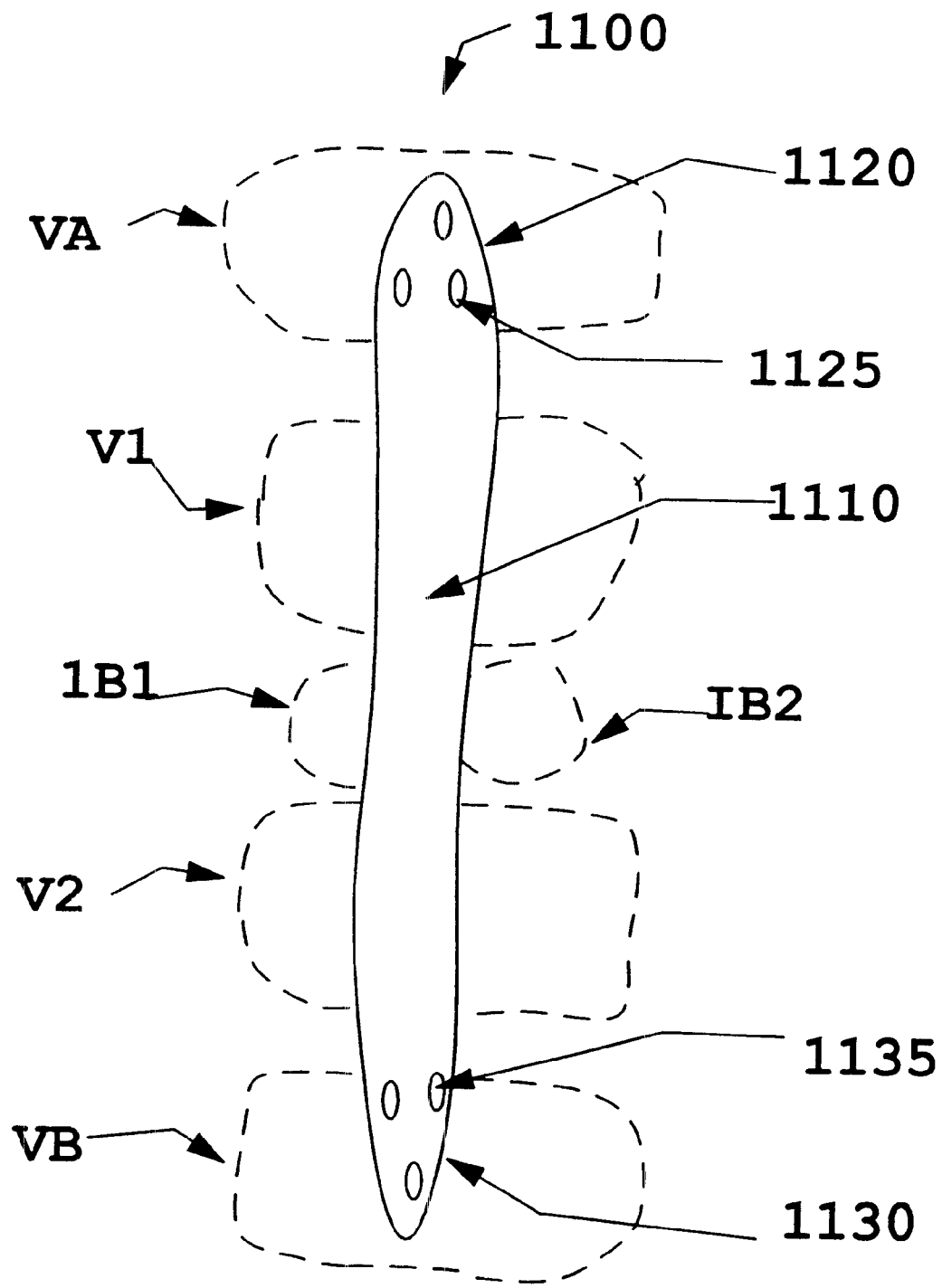
FIG. 11 depicts a band for limiting the motion and reducing the degradation of vertebrae juxtaposed to vertebrae undergoing fusion (i.e. as a spinal tension band) or for being affixed to any other anatomical structures to minimize motion of such structures in relation to each other.

In yet a further embodiment of the segmentally demineralized implant of this invention, there is provided a spinal tension band, STB. Typically, in spinal fusions, the motion segment adjacent to the fused segment (the juxtaposed discs) have been found to rapidly degrade. This degradation appears to be due to the hypermotion at these levels, due to the decreased motion at the juxtaposed fused segments. The STB of this invention assists in preventing this degradation and can avoid the need for further surgery, by spanning the fused segments and attaching to the juxtaposed vertebral body at the spinous process thereof. The STB may be used in any region of the spin, but is typically most useful for spanning fusions at two, three or more levels. The STB of this invention replaces or augments use of flexible stainless steel, titanium cables, elastomeric or polymeric synthetic materials currently in use. Accordingly, known techniques for attaching such devices to the spinous processes may be used, or the STB may be affixed to juxtaposed vertebral bodies in a fashion analogous to that described above for the ALL. In FIG. 11, there is disclosed one embodiment of the STB 1100 of this invention. As can be seen, the STB 1100 is affixed to a superior vertebrae, VA, and an inferior vertebra, VB, each of which are juxtaposed to a vertebrae V1 and V2, which are being fused to each other by means of interbody fusion devices IB1 and IB2. Intermediate portion 1110 of the STB may be demineralized, while the top portion 1120 and bottom portion 1130 may be retained in a mineralized or partially demineralized state. Fixation means 1125 and 1135 are provided for fixation of the STB to the juxtapose vertebrae VA and VB, respectively. Those skilled in the art will appreciate that this embodiment of the invention may be applied to any other anatomical structures to minimize motion of such structures in relation to each other. For example, the tension band of this invention may be utilized outside of the spinal context, such as for repair of a split sternum in a sternotomy.

Figure 12:
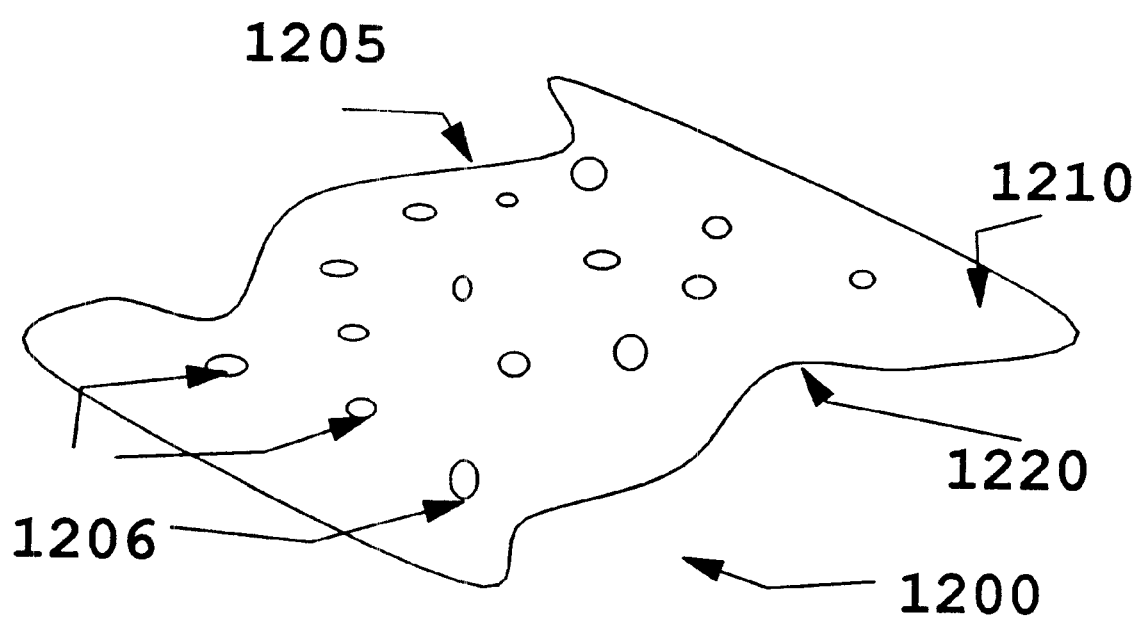
FIG. 12 depicts a perforated sheet comprising mineralized and demineralized bone for use as a "mesh", such as for use in a dressing or to retain particulate matter.

In FIG. 12, there is shown a further embodiment 1200 of the implant of this invention in the form of a sheet 1205 having a plurality of perforations 1206 comprising mineralized 1210 and demineralized 1220 segments. The perforated segmentally demineralized sheet of this embodiment of the invention may be used as a wrap or as a retention means for particulate material, gel material and the like when deposited on, in or around a bone, for example. Compositions which may be used in connection with this embodiment of the invention include osteogenic bone paste and the like.

Figure 13:
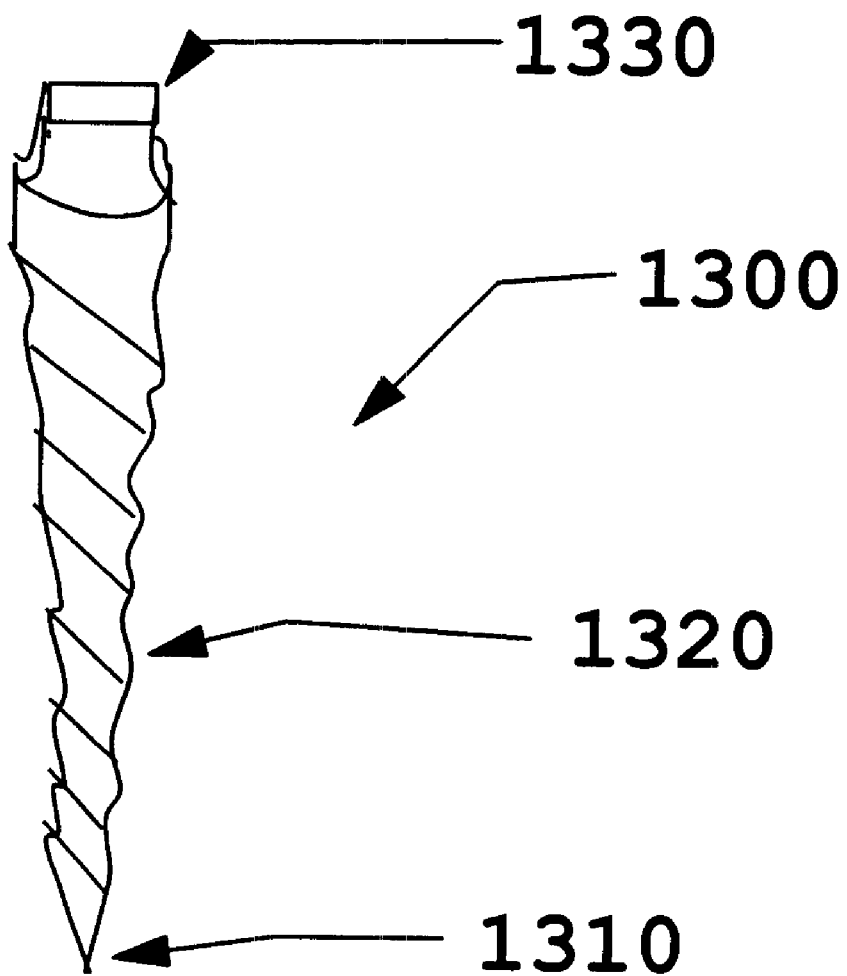
FIG. 13 depicts a cortical bone screw comprising at least a portion thereof which is demineralized or partially demineralized.

In FIG. 13 there is shown a further embodiment 1300 of the implant of this invention in the form of a screw made from cortical bone, comprising at least a portion thereof which is demineralized or partially demineralized. In this embodiment of the invention, desirable physical characteristics, and in vivo remodeling characteristics of such a device may be achieved by demineralizing or partially demineralizing various segments of the screw. Thus, for example, the point 1310 of the screw may be mineralized while the thread 1320 or drive head 1330 may be partially demineralized, to provide desirable surface characteristics, including but not limited to greater capacity for in vivo remodeling or minimized stress-fracture characteristics.

Having now generally described various embodiments of this invention, the following examples are provided by way of further exemplification of this invention. It should be recognized that the invention disclosed and claimed herein is not to be limited to the specifics provided in these examples, but is to be determined by the claims appended hereto:

EXAMPLE 1

Machining of the Implant of this Invention

The starting bone stock was chosen such that a piece of bone consisting substantially of cortical bone was used to machine the implant of this invention. Implants from the linea aspera of the femur or an anterior aspect of the tibia were used for this purpose, but other cortical sources of bone would be acceptable. The desired bone segment was removed with a bone saw or a water-cooled diamond core cutter, and trimmed to fit in a lathe for machining of desired external features. The bone was first machined to a known diameter and length. The ends were then machined to exhibit an internal thread, an external thread, or to have one machined end while the other end of the implant was drilled to exhibit one to several holes. The internal segment destined for demineralization was then either retained in a cylindrical form or machined in a milling machine or a grinder, to exhibit a flat internal segment, or another desired shape, between the threaded ends or the fixation ends.

EXAMPLE 2

Segmental Demineralization of Machined Bone Grafts

1. Large Cylindrical Ligament Repair Grafts

Demineralization of a machined large cylindrical ligament repair graft was completed in three days using approximately 40 mL of 0.75M–1.0M hydrochloric acid solution. The implant was exposed to fresh solution at least once per day. In order to produce a gradual transition from a fully mineralized end to a fully demineralized segment, the point of contact of the HCl solution with the implant was varied over the duration of the demineralization process.

2. Small Cylindrical Ligament Repair Grafts

Demineralization of a machined small cylindrical ligament repair graft was completed in two days using approximately 40 mL of 0.75M–1.0M hydrochloric acid solution. The implant was exposed to fresh solution at least once per day. In order to produce a gradual transition from a fully mineralized end to a fully demineralized segment, the point of contact of the HCl solution with the implant was varied over the duration of the demineralization process.

3. Flat Ligament or Tendon Repair Grafts

Demineralization of a machined ligament or tendon repair graft wherein an internal segment of the graft was machined flat, was completed in twenty-four hours using approximately 40 mL of 0.75M–1.0M hydrochloric acid solution. The implant was exposed to fresh solution at least once per day. In order to produce a gradual transition from a fully mineralized end to a fully demineralized segment, the point of contact of the HCl solution with the implant was varied over the duration of the demineralization process.

4. Double Flat Ligament Repair Grafts Having Two Rigid Ends

Demineralization of a machined, flat ligament repair graft was completed in twenty-four hours using approximately 40 mL of 0.75M–1.0M hydrochloric acid solution. The implant was exposed to fresh solution at least once per day. In order to produce a gradual transition from a fully mineralized end to a fully demineralized segment, the point of contact of the HCl solution with the implant was varied over the duration of the demineralization process. In order to protect both rigid ends of the implant, one bearing a thread and the other being a fixation block, the implant was exposed to the acid solution only in the middle segment by keeping the threaded end of the implant above the meniscus of the acid, and the fixation block end of the implant was inserted into a bored-out stopper, which also acted as a plug at the bottom of the acid container, into which a hole adequate to receive the implant bearing stopper had been drilled.

In view of the foregoing disclosure and examples, in which various embodiments of the implant of this invention are disclosed and described, including the best mode, the following claims are provided to define the scope of this invention. Those skilled in the art will recognize that various modifications on the specifics of the invention disclosed herein come within the scope of the appended claims.

EXAMPLE 3

ALL, STB, Craniomaxillofacial, and Bone-Wrap Implants

Following the procedures outlined in this disclosure, a flat cortical segment of bone is partially demineralized to form an ALL replacement or an STB, for stabilization of portions of the spine undergoing fusion. The ALL is affixed to two adjacent vertebrae undergoing fusion, while the STB is affixed to vertebrae juxtaposed to vertebrae undergoing fusion. The mineralized portion of the ALL and STB are utilized to affix the implants to the vertebrae by means of cortical bone screws, metallic pins or by hooking demineralized portions of the ALL or STB over vertebral processes. Craniomaxillofacial implantation of a pizza shaped implant such as that shown in FIG. 9 is achieved by resecting a portion of the skin and musculature above a craniomaxillofacial defect and laying the implant over the defect in a contoured fashion. The implant is maintained in place by repair of the superior skin and musculature. In the case of the bone-wrap, a sheet of cortical bone is segmentally masked such that adjacent liner segments of alternating mineralized and demineralized bone are produced upon contact of the masked bone to demineralizing agents such as acetic acid, hydrochloric acid, chelating agents, and the like. The bone-wrap is wrapped around a segment of fractured bone to provide support and to contain added osteogenic compositions to maximize repair of the fractured bone.

What is claimed is:

1. A biologically acceptable implant comprising a unitary segment of cortical bone having a machined mineralized first end, a machined mineralized second end, and a flexible portion of demineralized cortical bone there between connecting said first end to said second end.

2. The implant of claim 1, wherein said flexible portion of demineralized cortical bone acts as a hinge.

3. The implant of claim 1, wherein said machined mineralized first end and said machined mineralized second end are machined the same.

4. The implant of claim 1, wherein said machined mineralized first end and said machined mineralized second end are machined different.

5. The implant of claim 1, wherein said segment of cortical bone is autogenous.

6. The implant of claim 1, wherein said segment of cortical bone is allogenic.

7. The implant of claim 1, wherein said segment of cortical bone is a xenograft.

* * * * *